United States Patent [19]

Kobayashi et al.

[11] Patent Number: 5,654,019

[45] Date of Patent: Aug. 5, 1997

[54] BONE ENHANCING FACTORS FROM WHEY AND COMPOSITIONS CONTAINING THE SAME

[75] Inventors: Naomichi Kobayashi; Yukihiro Takada, both of Kawagoe; Masatoshi Yahiro, Higashimurayama, all of Japan

[73] Assignee: Snow Brand Milk Products Co., Ltd., Japan

[21] Appl. No.: 107,771

[22] PCT Filed: Dec. 25, 1992

[86] PCT No.: PCT/JP92/01699

§ 371 Date: Jan. 24, 1994

§ 102(e) Date: Jan. 24, 1994

[87] PCT Pub. No.: WO93/12807

PCT Pub. Date: Jul. 8, 1993

[30] Foreign Application Priority Data

Dec. 26, 1991 [JP] Japan ................................. 3-356754
May 4, 1992 [JP] Japan ................................. 4-142170

[51] Int. Cl.$^6$ .......................... A61K 38/02; A61K 35/20; A61K 38/00
[52] U.S. Cl. ................. 426/41; 424/535; 514/2; 426/590; 426/800; 426/807
[58] Field of Search ............................. 426/41, 590, 807, 426/800; 514/2; 424/535

[56] References Cited

U.S. PATENT DOCUMENTS

| | | | |
|---|---|---|---|
| 4,089,987 | 5/1978 | Chang | 426/564 |
| 4,143,174 | 3/1979 | Shah et al. | 426/570 |
| 4,209,503 | 6/1980 | Shah et al. | 424/49 |
| 5,028,436 | 7/1991 | Gauri | 426/491 |

FOREIGN PATENT DOCUMENTS

| | | | |
|---|---|---|---|
| 0 313 515 | 4/1989 | European Pat. Off. | A61K 35/20 |
| 890126062 | 5/1989 | Japan | A12C 21/00 |

OTHER PUBLICATIONS

Derwent ABS 92-265574/32 JP04183371 Jun. 30, 1992.

*Primary Examiner*—Herbert J. Lilling
*Attorney, Agent, or Firm*—Testa, Hurwitz & Thibeault, LLP

[57] ABSTRACT

The invention relates to an osteoblast growth and bone enhancing factor or factors having a molecular weight of about 5,000 to 28,000 daltons and an isoelectric point of 4 to 9, which is isolated from whey or whey protein. The invention includes various methods for obtaining the factor or factors from whey and whey protein. The factor or factors from whey and whey protein may be incorporated in foods, medicines and feeds for preventing or treating osteoporosis and other maladies in joints of bones.

10 Claims, 4 Drawing Sheets

BONE ENHANCING FACTORS FROM WHEY AND COMPOSITIONS CONTAINING THE SAME

1. FIELD OF THE INVENTION

This invention relates to an osteoblast growth and bone enhancing factor(s) derived from whey. Further, this invention relates to a bone enhancing factor(s) and foods containing the factor(s). Foods, feeds and medicines containing the factor(s) make bones of human who takes them strong and are useful for preventing or treating maladies in joints of bones and osteoporosis.

2. BACKGROUND OF THE INVENTION

Recently, the number of patients suffering from bone maladies such as osteoporosis, fracture and lumbago is increasing in proportion to increase of aged people. These bone maladies are mainly caused by lack of calcium intake, lowering of calcium absorbing ability, lack of secretion of active vitamin $D_3$, unbalance of hormones relating calcium metabolism and the like and the main causes are made clear as follows.

In bone tissues, bones are always destroyed, resorbed and created. At young ages, the bone resorption and formation are balanced, but the bone resorbing activity in the bone tissues becomes higher than the bone creating activity in proportion to aging (hereinafter called uncoupling) by various causes. When the uncoupling continues for a long time, the bone tissues become brittle and the above mentioned maladies are caused. Therefore, it is considered that the osteoporosis, fracture and lumbago can be prevented by preventing the uncoupling.

As treatments and prevention against the maladies in joints of bones and osteoporosis by preventing the uncoupling, (1) sufficient calcium supply by foods, (2) light exercises, (3) sun tan and (4) medical treatments have been performed in past.

For the calcium supply by foods, calcium salts such as calcium carbonate, calcium lactate, calcium phosphate and the like and natural calcium materials such as bovine bone powder, egg shell powder, fish bone powder and the like are used. However, some of these calcium salts become water insoluble in digestive organs and cannot be absorbed from intestines and absorbed calcium is not always used for bone formation, if bone creating activities are low.

For the light exercises, a light walk for around 30 minutes or the like is considered to be recommendable. However, as a body becomes weak, it becomes hard to do light exercises. Furthermore, it is almost impossible to do exercises for aged people who cannot even get up from a bed.

Sunlight promotes the biosynthesis of vitamin $D_3$ in the human body, but the supply of vitamin $D_3$ is not enough to prevent the uncoupling and to prevent maladies in joints of bones and osteoporosis.

For the medical treatments, medicines such as $1\alpha$-hydroxyvitamin $D_3$, calcitonin and the like are popularly known for bone enhancing ability themselves. However, these medicines consist of chemical compounds as effective components and are not food materials which can enhance bones by being taken safely in a mild condition for a long time.

As mentioned above, the food materials taken safely in a mild condition for a long time to enhance bones, whose effect is proved and established, are not known yet.

3. DISCLOSURE OF THE INVENTION

Milk is well known as a safe food to be taken for a long time and to enhance bones. The present inventors took notice of this nature of milk, assumed that there would be a factor(s) to enhance bones in milk, particularly whey and have been studying about the bone enhancing factor(s) in whey proteins. That is, the inventors have been trying to fractionate a protein fraction in milk, particularly whey and to extract a fraction having osteoblast growth and bone enhancing ability from the protein fraction. Consequently, the inventors found that a mixture of proteins and peptides obtained by treating a water soluble fraction of whey proteins with reverse osmosis (RO), electrodialysis (ED) or the like to remove salts contained in whey proteins had bone enhancing ability and applied the invention as Japanese Patent Application HEI 2-309504.

The inventors have been carrying out the fractionation of such whey proteins, found that the fraction clarified in physical properties by the further fractionation contained the factor(s) having osteoblast growth and bone enhancing ability and reached to the present invention.

Accordingly, the main object of the present invention is to separate and extract the fraction having bone enhancing ability from milk, particularly whey and to provide the osteoblast growth and bone enhancing factor(s).

The further object of this invention is to provide foods and drinks, medicines and feeds (hereinafter called foods and so on) containing the factor(s) which are capable of enhancing bones and preventing or treating maladies in joints of bones and osteoporosis.

As mentioned above, the inventors further tried to carry out the fractionation of whey proteins and found that the following fraction contained the osteoblast growth and bone enhancing factor(s). That is, this invention relates to the osteoblast growth and bone enhancing factor(s) shown as follows.

This invention provides the osteoblast growth and bone enhancing factor(s) existing in whey, which is obtained by precipitating whey or whey protein aqueous solution in a final ethanol concentration of more than 10% within the range of pH from 2 to 6 and has a molecular weight of 5,000 to 28,000 daltons (by SDS-polyacrylamide gel electrophoresis).

This invention also provides the osteoblast growth and bone enhancing factor(s) existing in whey, which is obtained by precipitating whey or whey protein aqueous solution in a final ethanol concentration of more than 10% within the range of pH from 2 to 6 and extracting a water soluble fraction from the precipitate and has a molecular weight of 5,000 to 28,000 daltons (by SDS-polyacrylamide gel electrophoresis).

Further, this invention relates to the following osteoblast growth and bone enhancing factor(s) mentioned below particularly.

This invention provides the osteoblast growth and bone enhancing factor(s) existing in whey, which is obtained by filtering whey or whey protein aqueous solution by an ultrafilter capable of fractionating substances with a molecular weight of more than 30,000 and extracting a water soluble fraction permeate and has a molecular weight of 5,000 to 28,000 daltons (by SDS-polyacrylamide gel electrophoresis) and an isoelectric point of 4 to 9.

This invention also provides the osteoblast growth and bone enhancing factor(s) existing in wheys which is obtained by heating wheys whey protein aqueous solution or its water soluble fraction permeated through an ultrafilter capable of fractionating substances with a molecular weight of more than 30,000, at 80° C. for 10 minutes and extracting a supernatant and has a molecular weight of 5,000 to 28,000 daltons (by SDS-polyacrylamide gel electrophoresis) and an isoelectric point of 4 to 9.

This invention further provides the osteoblast growth and bone enhancing factor(s) existing in whey, which is obtained by precipitating whey, whey protein aqueous solution or its water soluble fraction permeated through an ultrafilter capable of fractionating substances having a molecular weight of at more than 30,000, in a final NaCl concentration of more than 0.2M within the range of pH from 1.5 to 3.5 to produce a precipitate and extracting a water soluble fraction from the precipitate and has a molecular weight of 5,000 to 28,000 daltons (by SDS-polyacrylamide gel electrophoresis) and an isoelectric point of 4 to 9.

This invention still further provides the osteoblast growth and bone enhancing factor(s) existing in whey, which is obtained by heating whey or whey protein aqueous solution at 80° C. for 10 minutes so as not to produce a precipitate, filtering a supernatant by an ultrafilter capable of fractionating substances with a molecular weight of more than 30,000 and extracting a permeate and has a molecular weight of 5,000 to 28,000 daltons (by SDS-polyacrylamide gel electrophoresis) and an isoelectric point of 4 to 9.

This invention still further provides the osteoblast growth and bone enhancing factor(s) existing in whey, which is obtained by treating whey or whey protein aqueous solution in a final NaCl concentration of more than 0.2M within the range of pH from 1.5 to 3.5 to produce a precipitates filtering a water soluble fraction in the precipitate by an ultrafilter capable of fractionating substances with a molecular weight of more than 30,000 and extracting a permeate and has a molecular weight of 5,000 to 28,000 daltons (by SDS-polyacrylamide gel electrophoresis) and an isoelectric point of 4 to 9.

Furthermore, this invention relates to foods and drinks, medicines and feeds containing the osteoblast growth and bone enhancing factor(s).

The osteoblast growth and bone enhancing factor(s) of the present invention can be obtained by adding ethanol to whey or whey protein aqueous solution to produce a precipitate and extracting a water soluble fraction contained in the precipitate.

It is preferable to carry out the ethanol precipitation in a final ethanol concentration of more than 10% within the range of pH from 2 to 6 to obtain the fraction having a molecular weight of 5,000 to 28,000.

Further, the osteoblast growth and bone enhancing factor(s) can be obtained by heating whey or whey protein aqueous solution at 80° C. for 10 minutes, removing the formed precipitate and treating the resulting supernatant with an ultrafilter or other filters capable of fractionating substances with a molecular weight of more than 30,000 and extracting the fraction permeated. Also, the factor(s) can be obtained by treating whey or whey protein aqueous solution in a final NaCl concentration of more than 0.2M under an acidic condition, preferably pH 1.5~3.5, to produce a precipitate, extracting a water soluble fraction contained in the precipitate, treating the water soluble fraction with an ultrafilter or other filters capable of fractionating substances with a molecular weight of more than 30,000 and extracting the fraction permeated. Further, the factor(s) can be obtained by treating whey or whey protein aqueous solution with an ultrafilter capable of fractionating substances with a molecular weight of more than 30,000 to separate the fraction permeated and treating the fraction under heating or with NaCl. The thus obtained fraction has a molecular weight of 5,000 to 28,000 daltons (by SDS-polyacrylamide gel electrophoresis) and an isoelectric point of 4 to 9.

As will be detailed in the following examples, the fraction has osteoblast growth and bone enhancing ability and is regarded as the osteoblast growth and bone enhancing factor(s).

Further, this invention relates to foods and drinks, medicines and feeds containing the thus obtained osteoblast growth and bone enhancing factor(s).

A raw material of the osteoblast growth and bone enhancing factor(s) is milk.

Usable as milk in the present invention are fresh milk, milk powder, non-fat milk and reconstituted milk of cows, human beings, goats and sheeps. It is preferable to use whey proteins extracted from whey obtained from said milk.

The whey is transparent yellow-green liquid obtained by adding an acid or rennet to milk or non-fat milk and removing the formed coagulate and is obtained as a by-product of cheese or casein manufacturing. In the other hand, the whey proteins are produced by subjecting said whey to an ultrafiltration, reverse osmosis, chromatography, dimlysis and the like and contains whey protein concentrate having high protein content, obtained by removing lactose. The whey proteins to be used in the present invention may be a peptides or a hydrolyzed product of whey proteins by a protease.

In the present invention, the proteins and peptides obtained as a precipitate by fractionating whey proteins with ethanol is used and in the fractionation, the final concentration of ethanol is more than 10% and pH of the solution is 2 to 6, preferably.

For instance, the osteoblast growth and bone enhancing factor(s) of the present invention is produced as follows. Firsts whey or whey proteins (preferably whey protein concentrate or peptides obtained by hydrolyzing whey proteins with a protease or so on) is dissolved in water, pH of the solution is adjusted from neutral condition to acidic condition of 2 to 6 and ethanol is added to the solution so that the final concentration of ethanol becomes more thin 10%, preferably 10~60%, to produce a precipitate. The resulting precipitate can be used in the present invention and preferably, a water soluble fraction obtained by adding water to the precipitate is used to obtain the osteoblast growth and bone enhancing factor(s) having higher activity. Ordinarily, the water soluble fraction is lyophilized into powder. The water soluble fraction has the main band within the range of molecular weight from 5,000 to 28,000 by SDS-polyacrylamide gel electrophoresis.

Even when the precipitated fraction is hydrolyzed by a protease such as pepsin, trypsin, chymotrypsin or the like, the resulting hydrolysate product still has the osteoblast growth and bone enhancing ability.

Furthermore, the osteoblast growth and bone enhancing factor(s) of the present invention is contained in the supernatant obtained by heating said whey or whey protein aqueous solution at 80° C. for 10 minutes and removing the formed precipitate and is contained in a water soluble fraction of the precipitate obtained by treating said whey or whey protein aqueous solution in a final NaCl concentration of more than 0.2M within the range of pH from 1.5 to 3.5.

The present inventors examined the heat stability of whey or whey proteins by heat treatment. As the result, the osteoblast growth and bone enhancing activity was not reduced by the heat treatment at 80° C. for 10 minutes. However, the activity was reduced to approximately 85% by the heat treatment at 90° C. for 10 minutes and to approximately 70% by the heat treatment at 95° C. for 10 minutes. The osteoblast growth and bone enhancing factor(s) can be separated from other components in whey by using these properties of the heat stability. In other words, the heat unstable fraction can be removed as the precipitate by carrying out the heat treatment and pH value of the heat treatment, which can separate the heat unstable fraction effectively is 3.5 to 7.0.

NaCl treatment of the present invention can be carried out effectively within the range of pH from 1.5 to 3.5. In the fractionation by NaCl, the formation of precipitate is different according to each pH value, but the precipitate is formed in final NaCl concentration of more than 0.2M within the range of pH from 3.0 to 3.5. Other sodium salts, potassium salts, ammonium salts, phosphates, bivalent metal salts or the like may be used instead of NaCl and in these cases, the concentration of salts and pH value should be changed according to each condition.

It was found that the osteoblast growth and bone enhancing factor(s) of the present invention passed through an ultrafilter capable of fractionating substances with a molecular weight of more than 30,000. Usually, the resulting water soluble fraction is lyophilized into powder. The water soluble fraction has the main band within the range of molecular weight from 5,000 to 28,000 by SDS-polyacrylamide gel electrophoresis.

Even when the precipitated fraction is subjected to limitative hydrolysis by a protease such as pepsin, trypsin, chymotrypsin or the like, the resulting hydrolysate still has the osteoblast growth and bone enhancing ability.

In the present invention, the osteoblast growth and bone enhancing factor(s) can be contained in foods and so on.

It is preferable to add an absorptive calcium salt(s) such as calcium chloride, calcium carbonate, calcium lactate, natural calcium salt derived from egg shell or milk and others containing the same to the foods and so on containing the osteoblast growth and bone enhancing factor(s).

Further, the whey proteins or ethanol fractionation product thereof may be subjected to desalting treatment.

That is, the foods and so on of the present invention contain the fractionation product of whey proteins, desalted fraction or protease treated fraction thereof and the absorptive calcium salt (as the case may be).

As the foods and so on containing the osteoblast growth and bone enhancing factor(s) of the present invention, milk, juice, jelly, bread, noodles, soup, sausage, tablets and the like are exemplified. As the feeds, feed additives or other feeds and as the medicines, a tablet, granular agent, liquid agent and the like administrative orally are exemplified.

Human bones can be enhanced by taking foods and so on containing 100–500 mg of the osteoblast growth and bone enhancing factor(s) of the present invention per one day.

Acute toxicity was not recognized as the result of rat toxicity test, because the fraction was made from milk.

4. BRIEF DESCRIPTION OF THE DRAWINGS

FIG. 1 shows the osteoblast growth effect of ethanol fractionation product of whey proteins and peptides in Example 3. When the osteoblast growth activity in case of culturing osteoblast cells in a conventional medium only is assumed 100%, the osteoblast growth activity in case of adding the fractionation product of whey proteins in final ethanol concentration of 10, 20, 40 and 60% to the medium is shown.

5. BEST MODE FOR PRACTICE OF THE INVENTION

Figure 1:
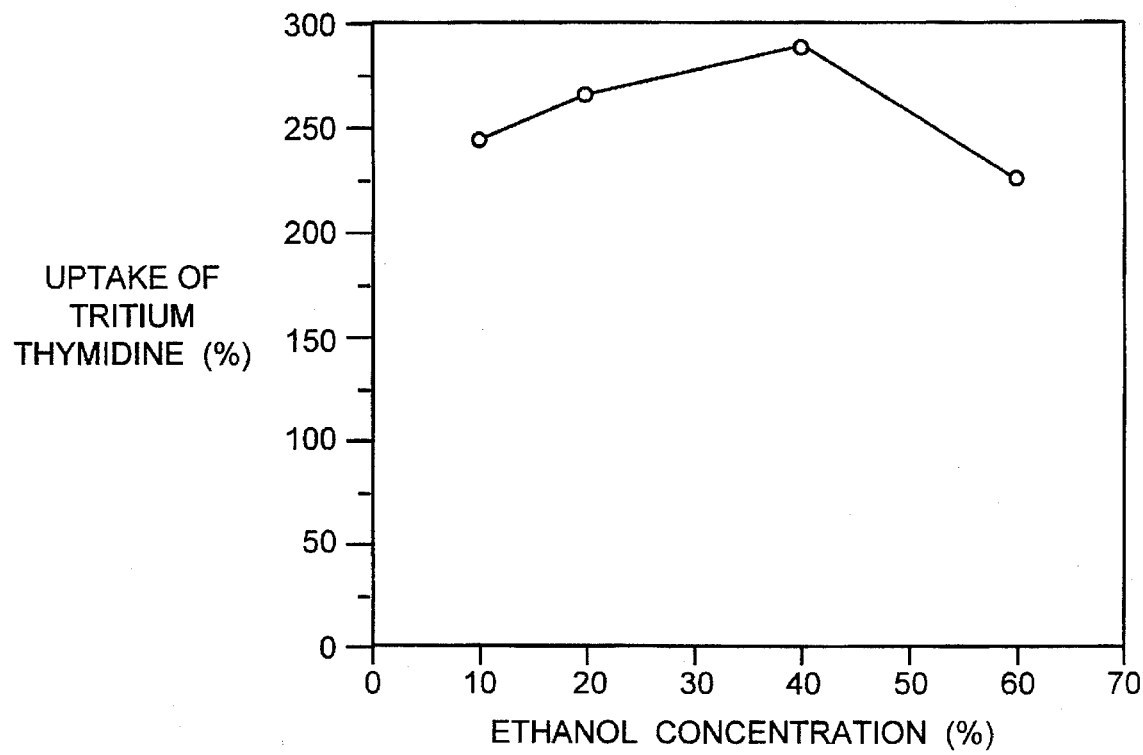

In the examples herein, the production of whey proteins of the present invention is described.

EXAMPLE 1.

PREPARATION OF ETHANOL FRACTIONATION PRODUCT OF WHEY PROTEINS FROM WHEY PROTEIN CONCENTRATE

Whey protein concentrate was dissolved in distilled water so as to give a concentration of 15%. To 3 l of the resulting solution, ethanol was added in the amount of 0.33 l, 0.75 l, 2 l and 4.5 l each so that the final concentration in the fractionation became 10%, 20%, 40% and 60% each. The mixed solution was stirred enough and left to stand at 4° C. for 3 days. The resulting solution was centrifuged at 2,500 G for 15 minutes to fractionate into supernatant and precipitate. To the precipitate, 500 ml of distilled water was added and the resulting solution was centrifuged at 2,500 G for 15 minutes to obtain a water soluble fraction. The fraction was lyophilized to obtain powder containing the ethanol fractionation product of whey proteins and peptides and the yield were 42 g, 23 g, 7 g and 6 g in ethanol concentration of 10%, 20%, 40% and 60%, respectively.

As the result of fractionating the powder by SDS-polyacrylamide gel electrophoresis, the main band was found within the range of molecular weight from 5,000 to 28,000 in all cases.

EXAMPLE 2

PREPARATION OF ETHANOL FRACTIONATION PRODUCT OF WHEY PROTEINS FROM UNPASTEURIZED WHEY 6N hydrochloric acid was added to 20 l of unpasteurized whey so as to adjust to pH 4. After adding 80 l of ethanol to the resulting solution, the solution was stirred enough and left to stand at 4° C. for 3 days. The thus prepared solution was centrifuged at 2,500 G for 15 minutes to fractionate into supernatant and precipitate. To the precipitate, 30 l of distilled water was added and the resulting solution was further centrifuged at 2,500 G for 15 minutes to obtain a water soluble fraction. The fraction was desalted and concentrated at the same time by reverse osmosis and lyophilized to obtain 42 g of powder containing the ethanol fractionation product of whey proteins and peptides.

As the result of fractionating the powder by BBS-polyacrylamide gel elecrophoresis, the main band was found within the range of molecular weight from. 5,000 to 28,000.

EXAMPLE 3

OSTEOBLAST GROWTH EFFECT OF ETHANOL FRACTIONATION PRODUCT OF WHEY PROTEINS AND PEPTIDES

Osteoblast cells (MC3T3-E1) were cultured with α-MEM (manufactured by Flow Labolatories) containing 0.3% of bovine blood serum using 96 well culture plate 10 µl of 5% aqueous solution of the powder obtained in Example 1 was added and the incubation was carried out for 18 hours. Thymidine labeled with tritium was added and the osteoblast growth activity was measured by radioactivity of thymidine absorbed into the osteoblast cells after 2 hours.

FIG. 1 shows the result of examination. The figure shows that the osteoblast growth activity measured by the radioactivity is increased when the ethanol fractionation product of whey proteins or peptides is added, as compared with no-addition of the ethanol fractionation product. In this case, the radioactivity in no-addition of the ethanol fractionation product is 100%. When the osteoblast cells were incubated with the ethanol fractionation product of whey proteins and peptides obtained in the final ethanol concentration of 10%~60%, the osteoblast growth activity was increased up to 200~300% as compared with the culture using the medium only. From the result, it is clear the ethanol fractionation product of whey proteins have osteoblast growth ability.

EXAMPLE 4

BONE ENHANCING ABILITY OF ETHANOL FRACTIONATION PRODUCT OF WHEY PROTEINS AND PEPTIDES

Table 1 shows a composition of foods given to experimental animals.

TABLE 1

| Composition of foods used for experiment (g/100 g) | | |
|---|---|---|
| | Sham & Control group | Whey protein group |
| Sucrose | 49.3 | 49.3 |
| Casein | 20 | 18 |
| Corn starch | 15 | 15 |
| Cellulose | 5 | 5 |
| Corn oil | 5 | 5 |
| Vitamins (containing choline) | 1.2 | 1.2 |
| Minerals | 4.5 | 4.5 |
| Ethanol fractionation product of whey proteins | — | 2 |

As shown in Table 1, 2 g of the ethanol fractionation product of whey proteins obtained in Example 2 was added to foods to replace 20 g of casein with 18 g. Calcium and phosphate were added 300 mg/100 g to all foods. The ratio of calcium and phosphate was controlled to be 1:1.

SD female rats (7 weeks after birth) were used as experimental animals. Osteoporosis model rats (OVX rats) were oophorectomized and fed by low calcium foods for a month. At the same time, 7 Sham rats were operated in the same way as above without taking out ovaries (pretended operation). Experiments were carried out by 7 rats as one group each.

One group of the osteoporosis model rats was fed by control foods and another group was fed by foods containing the ethanol fractionation product of whey proteins, shown in Table 1 supra, for a month.

Figure 2:
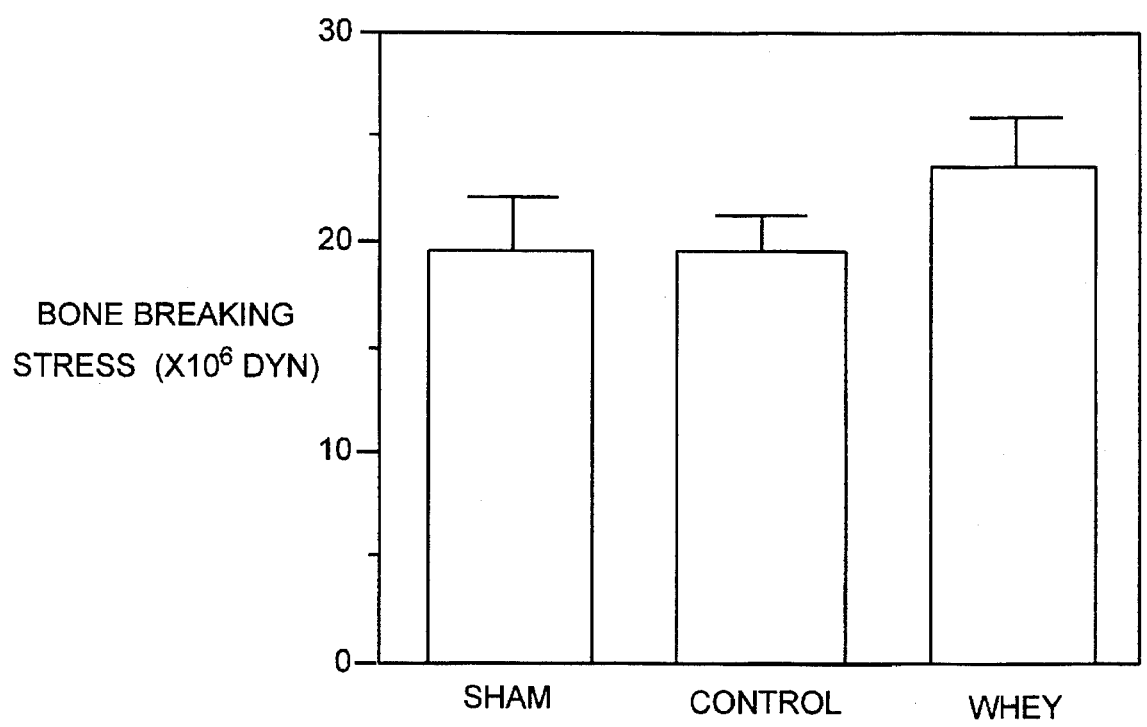
FIG. 2 shows the bone enhancing ability of ethanol fractionation product of whey proteins and peptides in Example 4. The result of measuring bone breaking stress against rat femurs is shown.
Figure 3:
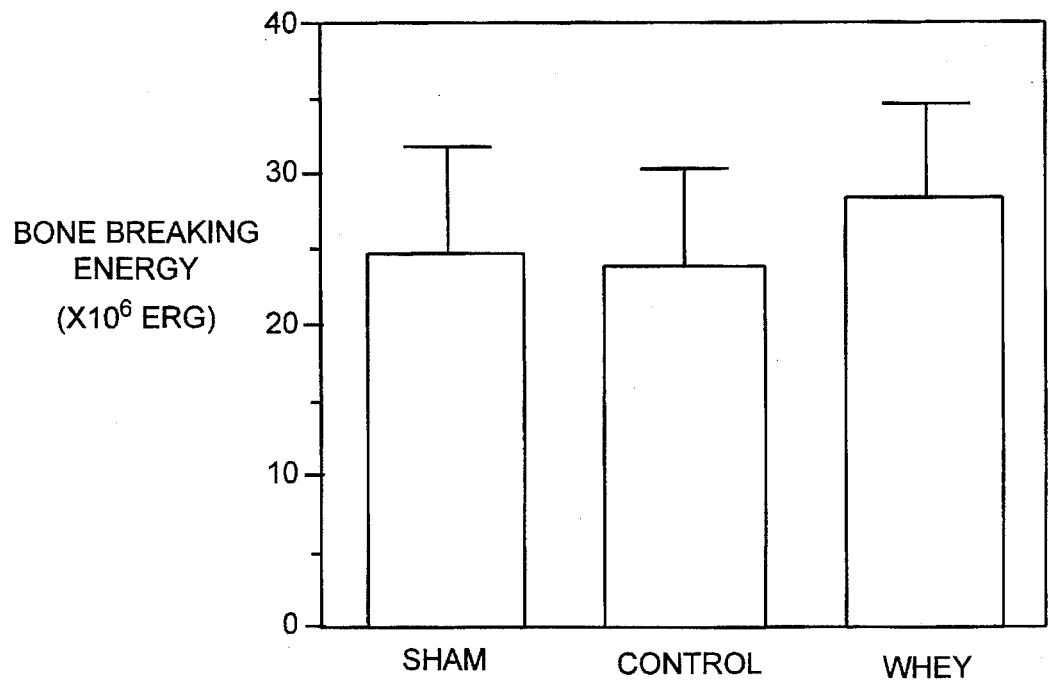
FIG. 3 shows the bone enhancing ability of ethanol fractionation product of whey proteins and peptides in Example 4. The result of measuring bone breaking energy against rat femurs is shown.

After a month, femurs of all rats in each group were taken out and the bone strength of them was measured using a breaking force measuring equipment. The result was shown in FIGS. 2 and 3. As shown in FIG. 2, the bone breaking stress of the rat group fed by whey protein foods was significantly higher than the group fed by control foods. The bone breaking energy was also high value as shown in FIG. 3. From the result, it is clear that the ethanol fractionation product of whey proteins have bone enhancing ability. Next, foods containing the ethanol fractionation product of whey proteins obtained in Example 2 are detailed in the following examples.

EXAMPLE 5

DRINKS CONTAINING ETHANOL

| FRACTIONATION PRODUCT OF WHEY PROTEINS | |
|---|---|
| | (weight %) |
| High fructose corn syrup | 15.0 |
| Juice | 10.0 |
| Citric acid | 0.5 |
| Ethanol fractionation Product of whey proteins | 0.5 |
| Flavor | 0.1 |
| Calcium | 0.1 |
| Water | 73.8 |

The above components were mixed, filled in a container and pasteurized by heating to obtain drinks by a conventional method.

EXAMPLE 6

TABLETS CONTAINING ETHANOL

| FRACTIONATION PRODUCT OF WHEY PROTEINS | |
|---|---|
| | (weight %) |
| Water containing crystalline glucose | 73.5 |
| Ethanol fractionation product of whey proteins | 20.0 |
| Calcium | 5.0 |
| Sugar ester | 1.0 |
| Flavor | 0.5 |

The above components were mixed and pressed to make tablets by a conventional method.

EXAMPLE 7

15 kg of whey protein concentrate was dissolved in water to prepare 100 l of the whey protein solution. The resulting solution was adjusted to pH 4.5 and heated by steam at 80° C. for 10 minutes. The solution was centrifuged at 5,000 G for 10 minutes to remove the precipitate and to obtain 80 l of the solution. 10 l of the solution was lyophilized to obtain 530 g of powder (Fraction A). Separately, 35 l of the remaining solution was adjusted to pH 3.0 and after adding NaCl so as to give a concentration of 0.2M, centrifuged at 15,000 G for 10 minutes to remove the precipitate. A NaCl concentration of the resulting supernatant was adjusted to 2.0M and the formed precipitate was collected by a centrifugal separation at 15,000 G for 10 minutes. The precipitate was suspended in 20 l of distilled water and 10 l of the resulting solution was desalted by reverse osmosis (RO) and lyophilized to obtain powder (Fraction B). 10 l of the remaining solution was filtered by an ultrafilter (manufactured by DDS Ltd.) capable of fractionating substances with a molecular weight of 100,000 and the permeate was filtered again by an ultrafilter capable of fractionating substances with a molecular weight of 30,000. The resulting permeate was desalted by electrodialysis and lyophilized to obtain powder (Fraction C). The yield of Fraction B and of Fraction C were 1,227 g and 540 g, respectively.

EXAMPLE 8

7.5 kg of whey protein concentrate was dissolved in water so as to give a total amount 50 l and the solution was adjusted to pH 4.5 and heated by steam at 80° C. for 10 minutes. The resulting solution was filtered by an ultrafilter (manufactured by DDS Ltd.) capable of fractionating substances with a molecular weight of 500,000 and a half amount (30l) of the permeate was desalted by reverse osmosis (RO) and lyophilized to obtain powder (Fraction D). 30 l of the remaining permeate was adjusted to pH 3.5 and after adding NaCl so as to give a final concentration of 0.3M, centrifuged at 15,000 G for 10 minutes to remove the formed precipitate. The resulting supernatant was adjusted to NaCl concentration of 2.0M and centrifuged at 15,000 G for 10 minutes. The resulting precipitate was separated and lyophilized to obtain powder (Fraction E). The yield of Fraction D and of Fraction E were 632 g and 235 g, respectively.

EXAMPLE 9

Hydrochloric acid was added to 200 l of non-fat milk till pH of the non-fat milk became 4.7 to precipitate casein and the solution was centrifuged at 5,000 G for 20 minutes to obtain 185 l of whey. The whey was filtered by an ultrafilter (manufactured by DDS Ltd.) capable of fractionating substances with a molecular weight of 500,000 and the resulting permeate was further filtered by an ultrafilter capable of fractionating substances with a molecular weight of 30,000 to carry out the desalting and concentration and to obtain 6 l of concentrate. 2 l of the concentrate was lyophilized as it was to obtain powder (Fraction F). 2 l of the concentrate was heated at 80° C. for 10 minutes under pH 6.3 and centrifuged at 5,000 G for 10 minutes. The resulting supernatant was lyophilized to obtain powder (Fraction G). 2 l of the remaining concentrate was adjusted to pH 1.5 and a NaCl concentration of 3M and centrifuged at 15,000 G for 10 minutes. The resulting precipitate was dissolved in water and the solution was desalted by electrodialysis and lyophilized to obtain powder (Fraction H). The yield of Fraction F, of Fraction H and of Fraction G were 340 g, 188 g and 202 g, respectively.

EXAMPLE 10

5.0 kg of whey protein concentrate was dissolved in 50 l of water and the solution was adjusted to pH 3.5 and a final NaCl concentration of 3.0M. The formed precipitate was recovered by a centrifugal separation at 15,000 G for 10 minutes and dissolved in 10 l of water. 2 l of the resulting solution was electrodialyzed and lyophilized to obtain powder (Fraction I). 8 l of the remaining solution was adjusted to pH 4.5 and heated at 80° C. for 10 minutes. A half amount of the heat-treated solution was centrifuged at 5,000 G for 10 minutes and the resulting supernatant was lyophilized to obtain powder (Fraction J). The remaining heat-treated solution was filtered by an ultrafilter capable of fractionating substances with a molecular weight of 500,000 and the permeate was desalted by reverse osmosis (RO) and lyophilized to obtain powder (Fraction K). The yield of Fraction I, of Fraction J and of Fraction K were 430 g, 255 g and 178 g, respectively.

EXAMPLE 11

2.5 kg of whey protein concentrate was dissolved in 50 l of water and the solution was adjusted to pH 3.0 and a final NaCl concentration of 3.0M. The formed precipitate was recovered by a centrifugal separation at 15,000 G for 10 minutes and dissolved in 10 l of water. The solution was filtered by an ultrafilter capable of fractionating substances with a molecular weight of 500,000. A half amount of the resulting permeate was desalted by reverse osmosis (RO) and lyophilized to obtain powder (Fraction L). The remaining permeate was heated at 80° C. for 10 minutes and centrifuged at 5,000 G for 10 minutes and the resulting supernatant was lyophilized to obtain powder (Fraction M). The yield of Fraction L and of Fraction M were 216 g and 175 g, respectively.

EXAMPLE 12

Lyophilized Fractions A~M obtained in Examples 7~11 were fractionated by SDS-polyacrylamide gel electrophoresis. The main band was found within the range of molecular weight from 5,000 to 28,000 in all cases. The same Fractions were subjected to isoelectric electrophoresis and the main band was found within the range of isoelectric point from 4 to 9 in all cases.

EXAMPLE 13

OSTEOBLAST GROWTH EFFECT OF FRACTIONS A~M OBTAINED IN EXAMPLES 7~11

Osteoblast cells (MC3T3-E1) were cultured with α-MEM (manufactured by Flow Labolatories) containing 0.3% of bovine blood serum using 96 well culture plate.

Fractions A~M obtained in Examples 7~11, in particular were particularly added to the wells so that the final concentration became 5 μg/ml and 50 μg/ml and the incubation was carried out for 18 hours. Thymidine labeled with tritium was added and each osteoblast growth activity was measured by radioactivity of thymidine absorbed into the osteoblast cells after 2 hours.

Figure 4:
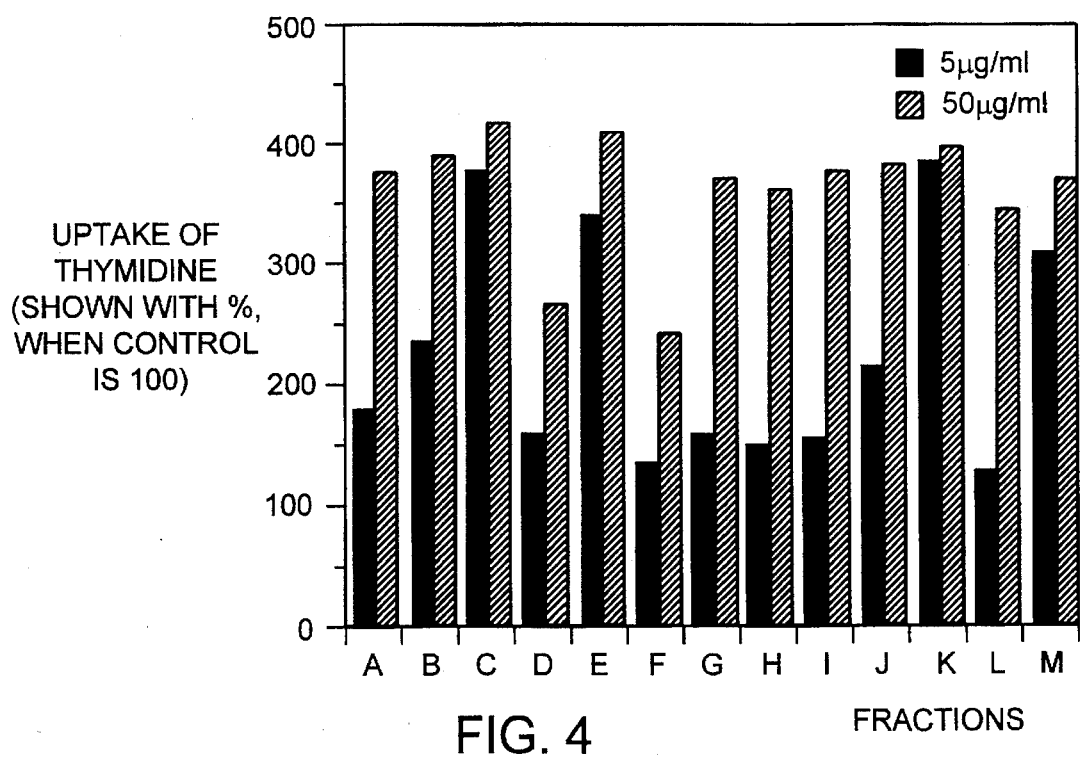
FIG. 4 shows the osteoblast growth effect in Example 13.

FIG. 4 shows the result of examinations. The figure shows that the osteoblast growth activity measured by the radioactivity is increased when Fractions A~M, in particular are added, as compared with no-addition of Fractions A~M. In this case, the radioactivity in no-addition of Fractions A~M is 100%.

When the osteoblast cells were incubated with Fractions A~M having the final concentration of 50 μg/ml, the osteoblast growth activity was increased up to 150~420% as compared with the culture using the medium only. Even when the final concentration was 5 μg/ml, the osteoblast growth activity was also observed. From the result, it is clear that Fractions A~M obtained in Examples 7~11 have osteoblast growth activity.

The same result was obtained when osteoblast cells (UMR 106) were cultured with Fractions A~M in the same way as above.

EXAMPLE 14

EFFECT OF STIMULATING COLLAGEN SYNTHESIS

Osteoblast cells (MC3T3-E1) were cultured with the same medium as Example 13. Fractions A~M obtained in Examples 7~11, in particular were particularly added so as to give a final concentration of 50 μg/ml and the incubation was carried out at 37° C. for 3 days. An amount of synthesized collagen was measured. The amount of collagen was measured by determinating hydroxyproline. The determination of hydroxyproline was carried out by adding p-dimethylaminobenzaldehyde to the collapsed cell hydrolyzed solution suspended using 6N hydrochloric acid.

Figure 5:
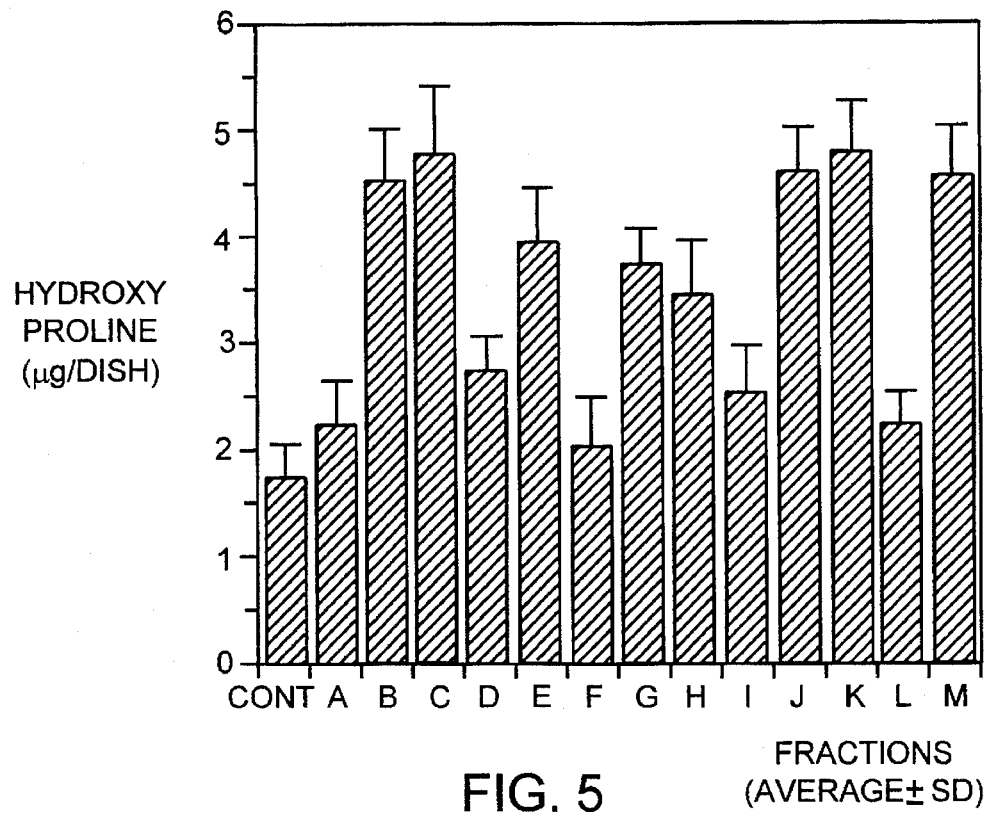
FIG. 5 shows the acceleration effect of collagen synthesis in Example 14.

FIG. 5 shows the result of examinations. The figure shows that the amount of hydroxyproline is increased when Fractions A~M obtained in Examples 7~11, in particular are particularly added, as compared with the culture using the medium only. From the result, it is clear the collagen synthesis in osteoblast cells is stimulated by the addition of Fractions A~M.

EXAMPLE 15

BONE ENHANCING ACTIVITY

Fractions C, E, K and M, in particular were particularly replaced with casein as shown in Table 2, infra, at the amount of 2 g to prepare foods. Calcium and phosphate Were added to all foods at 300 mg/100 g respectively foods each and the ratio of calcium and phosphate was controlled to be 1:1.

SD female rats (7 weeks after birth) were used as experimental animals. Osteoporosis model rats were oophorectomized and fed by low calcium foods for a month. At the same time, 7 Sham rats were operated in the same way as above without taking out ovaries (pretended operation). Experiments were carried out by 7 rats as one group Experiments were carried out by 7 rats as one group each.

Osteoporosis model rats were fed by each feeds as shown in Table 2, infra.

After a month, femurs of all rats in each group were taken out and the bone strength of them was measured using a breaking force measuring equipment.

TABLE 2

Composition of feeds used in examinations (g/100 g)

|  | Control | Sham | Fraction C | E | K | M |
|---|---|---|---|---|---|---|
| Sucrose | 49.3 | 49.3 | 49.3 | 49.3 | 49.3 | 49.3 |
| Casein | 20.0 | 20.0 | 18.0 | 18.0 | 18.0 | 18.0 |
| Corn starch | 15.0 | 15.0 | 15.0 | 15.0 | 15.0 | 15.0 |
| Cellulose | 5.0 | 5.0 | 5.0 | 5.0 | 5.0 | 5.0 |
| Corn oil | 5.0 | 5.0 | 5.0 | 5.0 | 5.0 | 5.0 |
| Vitamins (containing choline) | 1.2 | 1.2 | 1.2 | 1.2 | 1.2 | 1.2 |
| Minerals | 4.5 | 4.5 | 4.5 | 4.5 | 4.5 | 4.5 |

TABLE 2-continued

Composition of feeds used in examinations (g/100 g)

|  | Control | Sham | Fraction C | E | K | M |
|---|---|---|---|---|---|---|
| Fraction |  |  |  |  |  |  |
| C |  |  | 2.0 |  |  |  |
| E |  |  |  | 2.0 |  |  |
| K |  |  |  |  | 2.0 |  |
| M |  |  |  |  |  | 2.0 |

Figure 6:
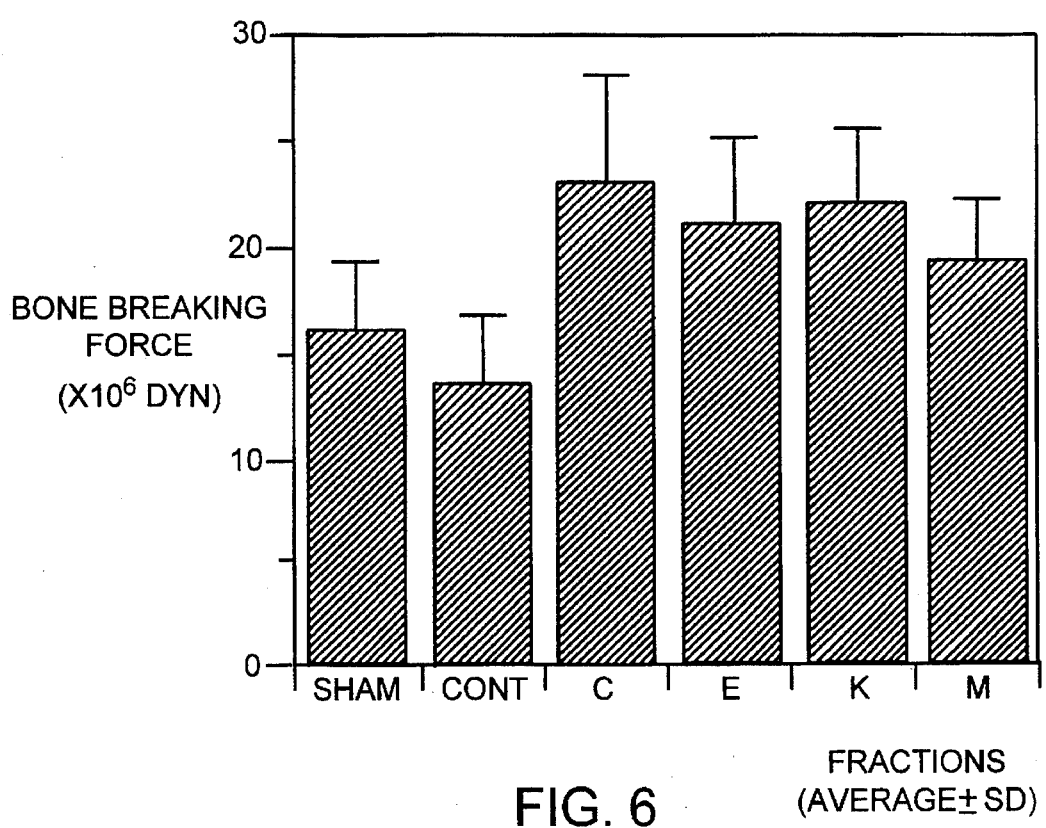
FIG. 6 shows the bone breaking force of osteoporosis model rats in Example 15.
Figure 7:
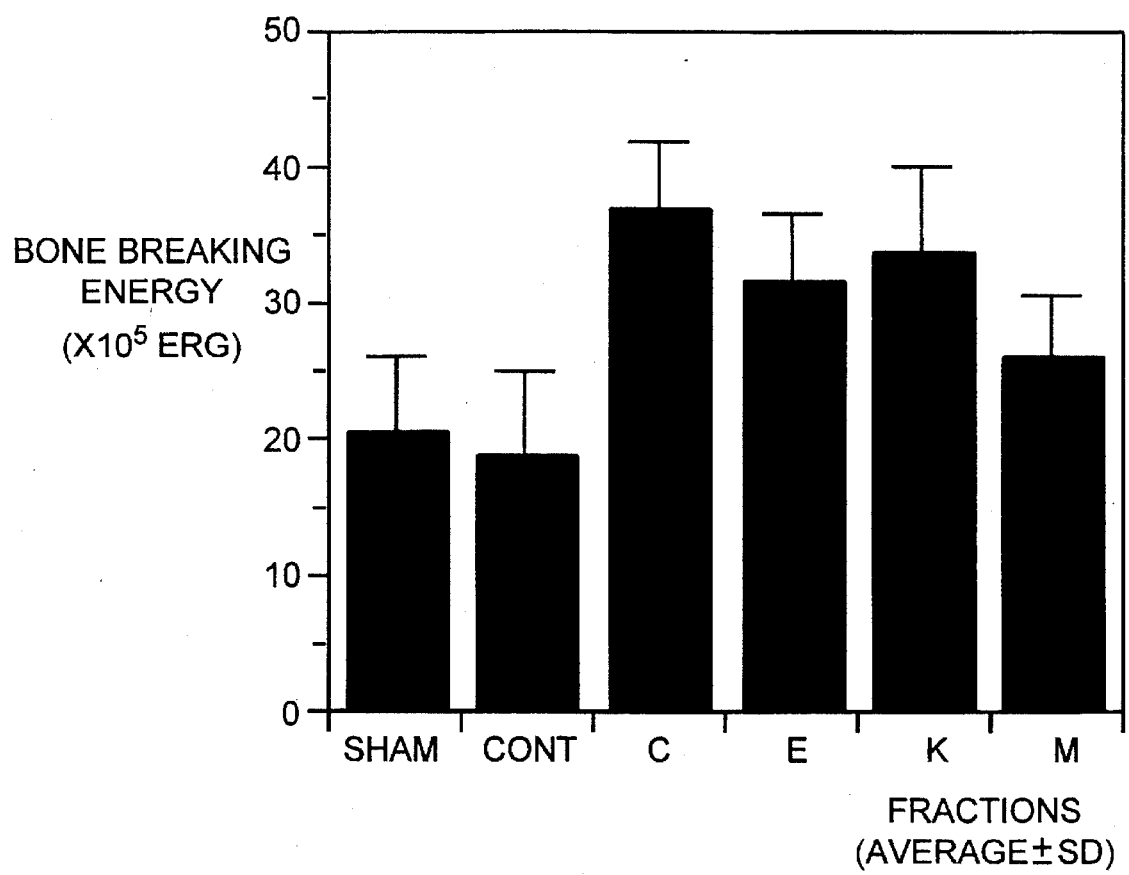
FIG. 7 shows the bone breaking energy of osteoporosis model rats in Example 16.

The result of the examinations is shown in FIGS. 6 and 7. As shown in FIG. 6, the bone breaking force of the rats fed by foods containing Fraction C, E, K or M were significantly higher than the rats fed by control foods. The bone breaking energy was also high value in Fraction C, E, K and M groups as shown in FIG. 7. From the result, it is clear that the Fraction C, E, K and M have bone enhancing ability.

Next, foods containing Fraction B obtained in Example 7 are detailed in the following examples.

EXAMPLE 16

DRINKS

| Component | weight % |
|---|---|
| High fructose corn syrup | 15.0 |
| Juice | 10.0 |
| Citric acid | 0.5 |
| Fraction B | 0.5 |
| Flavor | 0.1 |
| Calcium | 0.1 |
| Water | 73.8 |

The above components were mixed, filled in a container and pasteurized by heating to manufacture drinks by a conventional method.

EXAMPLE 17

TABLETS

| Component | weight % |
|---|---|
| Water containing crystalline glucose | 73.5 |
| Fraction B | 20.0 |
| Calcium | 5.0 |
| Sugar ester | 1.0 |
| Flavor | 0.5 |

The above components were mixed and pressed to make tablets by a conventional method.

6. INDUSTRIAL APPLICABILITY

Foods and the like containing the osteoblast growth and bone enhancing factor(s) of the present invention have bone enhancing ability and are useful for preventing or treating various maladie in joints of bones and osteoporosis.

What is claimed is:

1. A process for obtaining an osteoblast growth and bone enhancing factor from whey, said process comprising; contacting whey or an aqueous solution of whey protein with an aqueous solution comprising at least 10% by weight ethanol and having a pH in the range of from about 2 to about 6, thereby causing precipitation of said factor from the whey or whey protein solution; and separating said precipitated factor from said solution;

wherein said factor has a molecular weight of from about 5,000 to about 28,000 daltons as determined by SDS-PAGE.

2. A process for obtaining an osteoblast growth and bone enhancing factor from whey, said process comprising the steps of:

a. precipitating whey or an aqueous solution of whey protein by contacting said whey or solution of whey protein with a solution containing a ethanol concentration of more than about 10% ethanol and having a pH in the range of from about 2 to about 6 thereby causing formation of a precipitate containing said factor; and b. separating said factor from the precipitate by extracting a water soluble fraction from the precipitate containing said factor;

wherein said factor has a molecular weight of from about 5,000 to about 28,000 daltons as determined by SDS-PAGE.

3. A process for obtaining osteoblast growth and bone enhancing factor existing in whey, said process comprising the steps of:

a. filtering whey or an aqueous solution of whey protein with an ultrafilter having a molecular weight cut-off of about 30,000 thereby forming a permeate containing said factor; and b. separating said factor from the permeate by extracting a water soluble fraction from the permeate containing said factor;

wherein said factor has a molecular weight in the range of about 5,000 to about 28,000 daltons as determined by SDS-PAGE and an isoelectric point in the range of from about 4 to about 9.

4. A process for obtaining osteoblast growth and bone enhancing factor from whey, said process comprising the steps of:

a. heating whey, an aqueous solution of whey protein or a water-soluble fraction obtained by extracting with water a permeate formed by filtering whey through an ultrafilter having a molecular weight cut-off of about 30,000, at a temperature of about 80° C. for about 10 minutes thereby forming a precipitate and supernatant; and b. extracting the factor from the supernatant by contacting the supernatant with water;

wherein said factor has a molecular weigh tin the range of from about 5,000 to about 28,000 daltons as determined by SDS-PAGE and an isoelectric point of about 4 to about 9.

5. A process for obtaining an osteoblast growth and bone enhancing factor from whey, said process comprising the steps of:

a. contacting whey, an aqueous solution of whey protein or a water-soluble fraction obtained by extracting with water a permeate formed by filtering whey through an ultrafilter having a molecular weight cut-off of about 30,000, with a sodium chloride solution having a sodium chloride concentration of at least about 0.2M and a pH of from about 1.5 to 3.5 to produce a precipitate; and b. extracting a water-soluble fraction containing said factor from the precipitate;

wherein said factor has a molecular weight in the range of from about 5,000 to about 28,000 daltons as determined by SDS-PAGE and an isoelectric point of about 4 to about 9.

6. A process for obtaining an osteoblast growth and bone enhancing factor from whey, said process comprising the steps of:

a. heating whey or an aqueous solution of whey protein at 80° C. for 10 minutes;

b. contacting the solution with an ultrafilter having a molecular weight cut-off of about 30,000 thereby forming a permeate containing said factor; and c. forming a water-soluble fraction containing said factor by extracting the permeate with water;

wherein said factor has a molecular weight in the range of from about 5,000 to about 28,000 daltons as determined by SDS-PAGE and an isoelectric point of about 4 to about 9.

7. A process for obtaining an osteoblast growth and bone enhancing factor from whey, said process comprising the steps of:

a. treating whey or an aqueous solution of whey protein with a sodium chloride solution having a sodium chloride concentration of at least about 0.2M and a pH of from about 1.5 to 3.5 to produce a precipitate;

b. forming a water-soluble fraction containing said factor by extracting said precipitate with water;

c. contacting said fraction with an ultrafilter having a molecular weight cut-off of about 30,000 thereby forming a permeate containing said factor; and d. extracting said permeate with water thereby forming a water-soluble fraction containing said factor;

wherein said factor has a molecular weight in the range of from about 5,000 to about 28,000 daltons as determined by SDS-PAGE and an isoelectric point of about 4 to about 9.

8. Bone enhancing foods and drinks containing the osteoblast growth and bone enhancing factor obtained by the process of any of claims 1 to 7.

9. A composition for preventing or treating a bone malady comprising the osteoblast growth and bone enhancing factor of any of claims 1 to 7 obtained by the process.

10. Bone enhancing feeds comprising the osteoblast growth and bone enhancing factor obtained by the process of any of claims 1 to 7.

\* \* \* \* \*